(12) United States Patent
Kogawa et al.

(10) Patent No.: US 7,232,222 B2
(45) Date of Patent: Jun. 19, 2007

(54) OPERATION MICROSCOPE

(75) Inventors: Taisaku Kogawa, Tokyo (JP); Nobuaki Kitajima, Tokyo (JP); Kazuyuki Okamura, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 585 days.

(21) Appl. No.: 10/778,336

(22) Filed: Feb. 17, 2004

(65) Prior Publication Data

US 2004/0183999 A1 Sep. 23, 2004

(30) Foreign Application Priority Data

Feb. 17, 2003 (JP) .............................. 2003-037646

(51) Int. Cl.
*A61B 3/10* (2006.01)
*A61B 3/14* (2006.01)
*G02B 21/00* (2006.01)
*G02B 21/06* (2006.01)

(52) U.S. Cl. ...................... 351/221; 351/216; 351/205; 351/206; 351/209; 359/381; 359/383; 359/385; 359/389; 359/368

(58) Field of Classification Search ................ 351/205, 351/206, 208–211, 216, 221, 233, 236, 377, 351/462; 359/368, 381, 383, 385, 387, 389, 359/390
See application file for complete search history.

(56) References Cited

U.S. PATENT DOCUMENTS

| 4,807,989 | A | * | 2/1989 | Nagano et al. ............. 351/212 |
|---|---|---|---|---|
| 4,838,671 | A | | 6/1989 | Papritz et al. .............. 359/377 |
| 4,932,774 | A | * | 6/1990 | Takagi et al. ............... 351/221 |
| 5,760,952 | A | | 6/1998 | Koetke ....................... 359/389 |
| 6,394,602 | B1 | * | 5/2002 | Morrison et al. ........... 351/206 |
| 6,634,749 | B1 | * | 10/2003 | Morrison et al. ........... 351/209 |
| 6,733,128 | B2 | * | 5/2004 | Kirchhuebel ................ 351/205 |
| 6,943,942 | B2 | * | 9/2005 | Horiguchi et al. ......... 359/381 |
| 7,072,104 | B2 | * | 7/2006 | Okamura et al. ........... 359/385 |
| 2002/0044256 | A1 | | 4/2002 | Kirchhuebel ................ 351/205 |
| 2002/0191280 | A1 | | 12/2002 | Horiguchi et al. .......... 359/383 |

FOREIGN PATENT DOCUMENTS

| JP | 2001-275978 | 10/2001 |
|---|---|---|
| JP | 2002-350735 | 12/2002 |

* cited by examiner

*Primary Examiner*—Loha Ben
(74) *Attorney, Agent, or Firm*—Armstrong, Kratz, Quintos, Hanson & Brooks, LLP

(57) ABSTRACT

Provided is an operation microscope where manipulations to be performed in response to switching between methods for observing an eye to be operated are performed in an interlocked manner, thereby improving manipulability. When recognizing that a change-over switch is switched to its upper position, a control circuit controls a drive apparatus so that an operator microscope is raised, controls a drive mechanism so that an optical unit is moved to an inverter-on position, changes the turned-on position of a light source so that an illumination light flux forms a small angle with respect to an observation optical axis, and controls a solenoid so that a stereo variator is moved to be arranged on an optical path of an observation light flux.

13 Claims, 14 Drawing Sheets

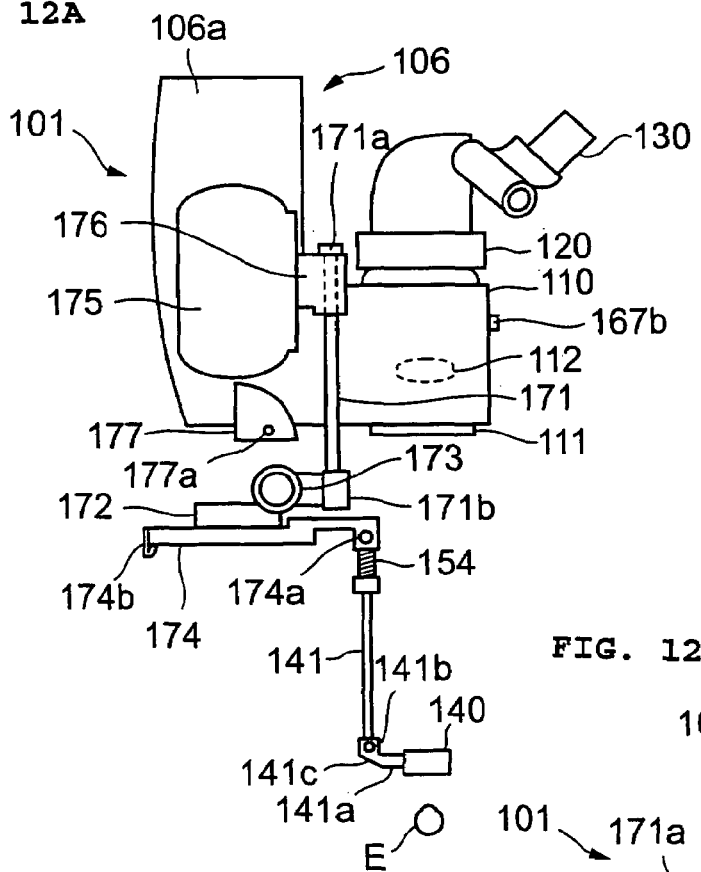
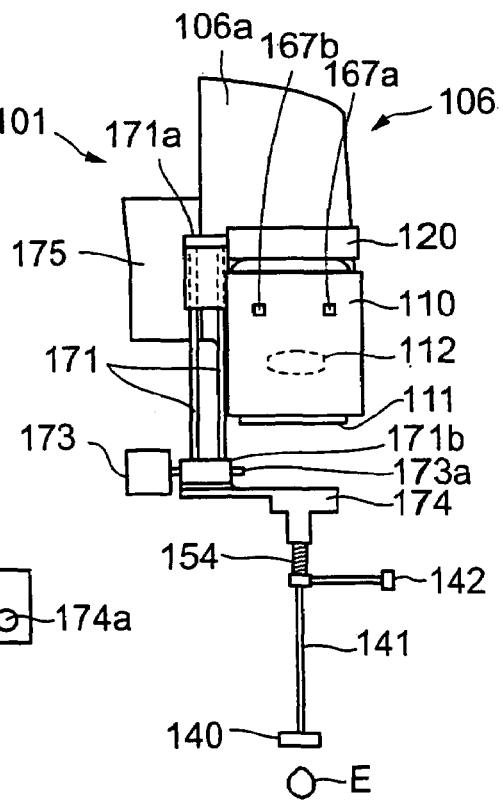
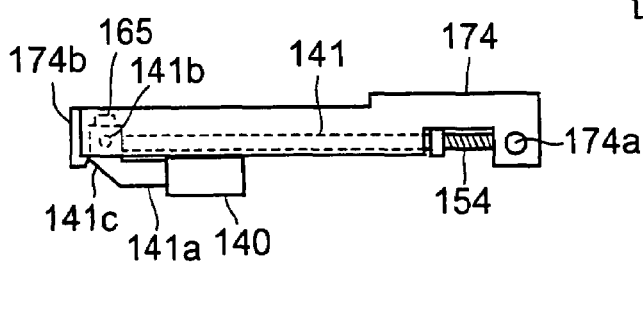

OPERATION MICROSCOPE

BACKGROUND OF THE INVENTION

1. Field of the Invention

The present invention relates to an operation microscope, and in particular to an operation microscope that is applicable to an ophthalmologic operation.

2. Description of the Related Art

With the recent advancement of the aging society and the like, there has been a growing demand for ophthalmologic operations than before. An eye (eye to be operated) of a patient that is the subject of an ophthalmologic operation has an extremely minute and delicate structure, so that it is common practice to conduct the operation while observing the eye to be operated using a microscope.

As an example of such an operation microscope, there is known a microscope disclosed in JP 2002-350735 A (hereinafter referred to as the "known document 1"), for instance. This operation microscope has a construction where a front lens for illuminating an eye to be operated is provided between an optical system including an objective lens and the eye to be operated, a lens unit for converting an inverted image of the eye to be operated obtained through the front lens into an erected image is provided so as to be insertable and removable from an optical path of the optical system, the moving direction of the front lens and the optical system by a moving apparatus is switched based on whether the lens unit is inserted onto the optical path. With this operation microscope, there is eliminated the necessity to hold a light guide in one hand unlike in the case of a conventional ophthalmologic operation, so that it becomes possible for an operator to freely use his/her both hands and to appropriately move the front lens and the optical system while observing the eye to be operated. Consequently, the accuracy and swiftness of an operation are improved.

Also, JP 2001-275978 A (hereinafter referred to as the "known document 2") discloses an ophthalmologic apparatus provided with a binocular stereomicroscope. This ophthalmologic apparatus has a construction allowing control so that depending on whether the anterior portion of an eye to be examined is to be observed or the retina or the vitreous body thereof is to be observed, a stereo angle conversion portion and a color temperature conversion portion are inserted/removed onto/from right and left optical axes by changing the position of a frame. In more detail, when the frame is set closer to the eye to be examined in order to observe the anterior portion, a position detection switch detects this situation and a control processing unit inserts the stereo angle conversion portion and the color temperature conversion element onto the right and left optical axes based on the detected result. On the other hand, when the frame is set away from the eye to be examined in order to observe the retina or the vitreous body, the position detection switch detects this situation and the control processing unit retracts the stereo angle conversion portion and the color temperature conversion element from the right and left optical axes based on the detected result.

Further, the ophthalmologic apparatus provided with the stereomicroscope described in the known document 2 is constructed so that whether an auxiliary lens (contact lens) for observing the eyefundus of the eye to be examined is inserted into the space between the eye to be examined and the objective lens is detected, and the insertion/removal of the stereo angle conversion portion and/or the color temperature conversion element onto/from the right and left optical axes is controlled based on the detected result.

In some cases, during an ophthalmologic operation, a microscope is used while performing switching between various observation modes. Therefore, the conventional operation microscope described above is constructed so that it is possible to insert/remove the front lens onto/from the optical path by swinging a holding arm depending on the purpose of usage. When it is desired to observe the retina or the vitreous body of the eye to be operated, for instance, the front lens is arranged between the objective lens and the eye to be operated and is used. On the other hand, at the time of observation of the anterior portion of the eye to be operated or at the time of use of the contact lens, for instance, it is required to swing and retract the front lens.

Also, at the time when the use/retraction of the front lens is switched, it is required to change the irradiation angle of an illumination light flux, to adjust the position of the objective lens with respect to the eye to be operated, and to switch the arrangement of the lens unit. Consequently, the operator is required to perform manipulations such as the changing of the irradiation angle of the illumination light flux, the insertion/removal of the lens unit onto/from the optical path, the adjustment of the position of the objective lens, and the like in accordance with the use/retraction of the front lens. Accordingly, it cannot be necessarily said that manipulability during an operation is favorable, and this becomes one factor that hinders the smooth conduct of the operation.

Further, with the conventional operation microscope described in the known document 1, the front lens can be inserted into the space between the eye to be operated and the objective lens under a state where the objective lens is positioned close to the eye to be operated. Also, the objective lens and the front lens can be set closer to the eye to be operated under a state where the front lens is inserted. Consequently, there is a danger that the front lens may hit the eye to be operated.

On the other hand, with the ophthalmologic apparatus provided with the stereomicroscope described in the known document 2, the control of the insertion/removal of the optical elements is performed only based on the detected result of the position of the frame or the position of the auxiliary lens and the optical elements, whose insertion/removal is controlled, are limited to the stereo angle conversion portion and the color temperature conversion element. Consequently, it is difficult to apply this technique to an operation microscope.

It is conceived that this is due to the following reason. The movement of the frame in the case of the ophthalmologic apparatus corresponds to the upward/downward movement of an optical system with respect to an eye to be operated in the case of an operation microscope, and this upward/downward movement of the optical system is performed in accordance with the presence or absence of a front lens (in response to switching between observation methods), whereby it is difficult to sufficiently enhance manipulability only through the control of the insertion/removal of the stereo angle conversion portion (stereo variator) and the color temperature conversion element. That is, in the case of the operation microscope, the upward/downward movement of the optical system is performed in accordance with the manual insertion/removal of the front lens in many cases and, in such cases, it is required to separately perform manipulation for upwardly/downwardly moving the optical system in addition to the insertion/removal of the front lens. Consequently, it is hard to say that excellent manipulability is attained.

SUMMARY OF THE INVENTION

The present invention has been made in view of the circumstances described above, and has an object to provide an operation microscope which enables interlocked execution of a series of manipulations that should be performed in response to switching between methods for observing an eye to be operated, thereby enhanced in manipulability.

Further, the present invention has an object to provide an operation microscope where safety is improved by enabling the prevention of an accident where a front lens hits an eye to be operated.

In order to attain the above-mentioned objects, according to a first aspect of the present invention, there is provided an operation microscope, including:

an objective lens set so as to confront an eye to be operated;

a front lens that is insertable and removable manually from a space between the eye to be operated and the objective lens and having a detecting means to detect the insertion and removal of the front lens;

an illumination means for generating an illumination light for illuminating the eye to be operated, the illumination means being capable of changing an angle of the illumination light flux with respect to an optical axis of an observation light flux used to observe the eye to be operated;

a control means for, based on a signal of an operation of the detecting means, controlling the illumination means in interlocking manner so as to observe the eye to be operated.

According to a second aspect of the present invention further includes, a moving means for moving the objective lens and/or the front lens in the axis direction of the eye to be operated, a switching means for driving the moving means, and the control means further controls the switching means and every means in interlocking manner so as to observe the eye to be operated.

Further, according to a third aspect of the present invention, the operation microscope according to the second aspect of the present invention further includes:

an optical unit for, when the front lens is inserted into the space between the eye to be operated and the objective lens, converting an inverted observation image of the eye to be operated into an erected image; and an optical unit insertion/removal means for inserting/removing the optical unit onto/from the optical path of the observation light flux from the eye to be operated, in which the control means controls, based on the operation of the switching means, further the insertion/removal of the optical unit onto/from the optical path of the observation light flux by the optical unit insertion/removal means.

Further, according to a fourth aspect of the present invention, the operation microscope according to the second aspect of the present invention further includes:

a pair of right and left eyepieces for observing the eye to be operated;

a pair of right and left optical systems that respectively guide the observation light from the eye to be operated to the pair of right and left eyepieces;

an optical axis position changing element for changing relative positions of optical axes of the observation light flux to be guided by the pair of right and left optical systems; and an optical axis position changing element insertion/removal means for inserting/removing the optical axis position changing element onto/from the optical path of the observation light flux, in which the control means controls, based on the operation of the detecting means, the insertion/removal of the optical axis position changing element onto/from the optical path of the observation light flux by the optical axis position changing element insertion/removal means.

Further, according to a fifth aspect of the present invention, the operation microscope according to the second aspect of the present invention further includes:

an optical unit for, when the front lens is inserted into the space between the eye to be operated and the objective lens, converting an inverted observation image of the eye to be operated into an erected image; and an optical unit insertion/removal means for inserting/removing the optical unit onto/from the optical path of the observation light flux from the eye to be operated, in which the control means controls, in accordance with the insertion/removal of the front lens, further the insertion/removal of the optical unit onto/from the optical path of the observation light flux by the optical unit insertion/removal means.

Further, according to a sixth aspect of the present invention, the operation microscope according to the second aspect of the present invention further includes:

a pair of right and left eyepieces for observing the eye to be operated;

a pair of right and left optical systems that respectively guide the observation light flux from the eye to be operated to the pair of right and left eyepieces;

an optical axis position changing element for changing relative positions of optical axes of the observation light flux to be guided by the pair of right and left optical systems; and an optical axis position changing element insertion/removal means for inserting/removing the optical axis position changing element onto/from the optical path of the observation light flux, in which the control means controls, in accordance with the insertion/removal of the front lens, further the insertion/removal of the pair of eyepieces, the pair of optical systems and the optical axis position changing element onto/from the optical path of the observation light flux.

Further, according to a seventh aspect of the present invention, the operation microscope according to the second aspect of the present invention, in which the control means controls, in accordance with insertion/removal of the front lens, further a direction of the movement of the objective lens and/or the front lens conducted by the movement means with respect to the eye to be operated.

Further, according to an eighth aspect of the present invention, in the operation microscope according to the second aspect of the present invention, the control means controls so that the insertion of the front lens into the space between the eye to be operated and the objective lens is prevented until the objective lens and the front lens are moved by the moving means in a direction in which the objective lens and the front lens are drawn away from the eye to be operated.

Further, according to a ninth aspect of the present invention, in the operation microscope according to the second aspect of the present invention, the control means controls so that the movement of the objective lens and the front lens conducted by the moving means in a direction, in which the objective lens and the front lens approach the eye to be operated, is further prevented until the front lens and the objective lens are retracted from between the eye to be operated and the objective lens.

Further, according to a tenth aspect of the present invention, the operation microscope according to the second aspect of the present invention further includes a front lens moving means for moving the front lens in an optical axis direction of the observation light flux, in which the control means controls, in accordance with the insertion/removal of the front lens, further the front lens moving means so that the front lens is returned to a predetermined initial position.

Further, according to an eleventh aspect of the present invention, the operation microscope according to the second aspect of the present invention further includes a zoom magnification changing means for changing a zoom magnification of an observation image of the eye to be operated, in which the control means controls, in accordance with the insertion/removal of the front lens, further the zoom magnification changing means so that the zoom magnification is returned to a predetermined initial magnification.

Further, according to a twelfth aspect of the present invention, the operation microscope according to any one of the second to eleventh aspects of the present invention further includes a detection means for detecting whether the front lens is received at a predetermined receipt position, in which the control means judges further the insertion/removal of the front lens based on a result of the detection by the detection means.

Further, according to thirteenth aspect of the present invention, the operation microscope according to any one of the first to twelfth aspects of the present invention, includes further a foot switch to operate every interlocking switching means.

BRIEF DESCRIPTION OF THE DRAWINGS

In the accompanying drawings:

FIG. 12A is an external side view showing a construction of an operator microscope of an operation microscope of a second embodiment according to the present invention;

FIG. 12B is an external front view showing the construction of the operator microscope of the operation microscope of the second embodiment according to the present invention;

FIG. 12C is a see-through side view showing a received mode of a front lens of the operator microscope of the operation microscope of the second embodiment according to the present invention;

DETAILED DESCRIPTION OF THE PREFERRED EMBODIMENTS

<First Embodiment>

(Construction of Operator Microscope)

Figure 1:
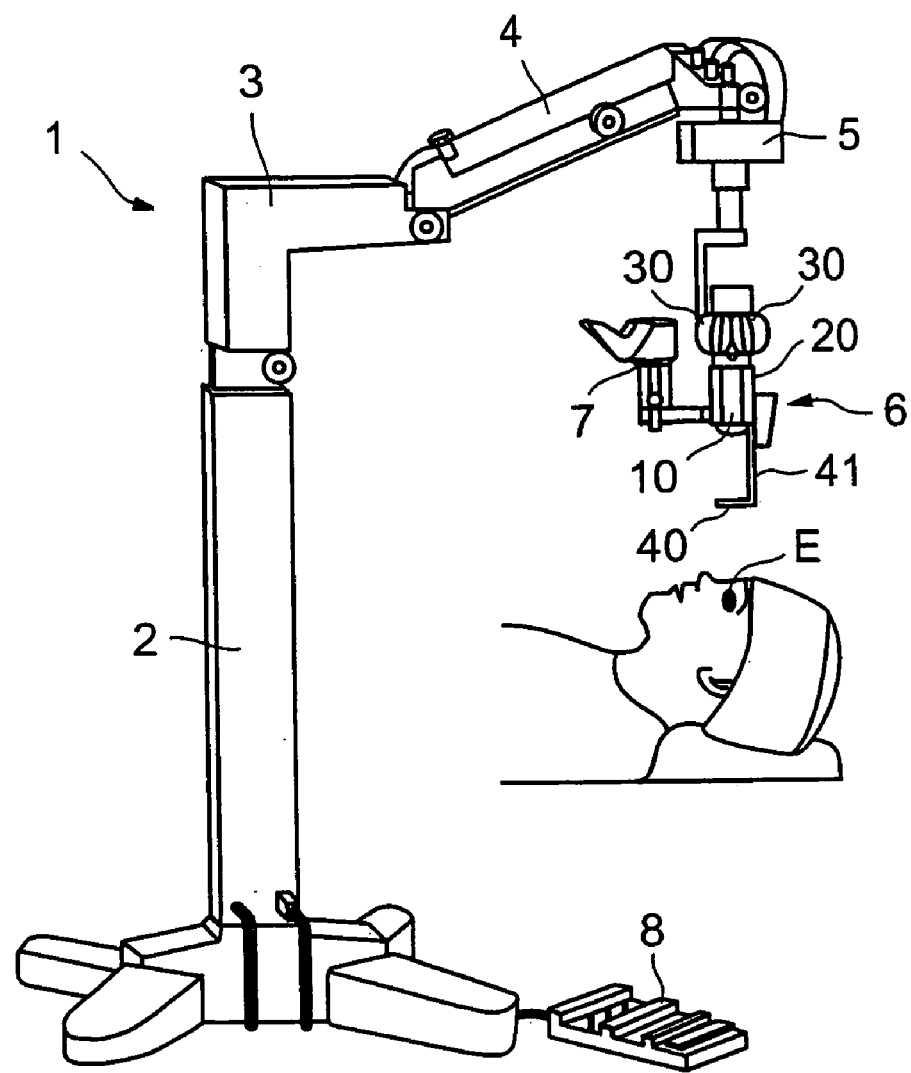
FIG. 1 is a schematic diagram showing an overall construction of an operation microscope of a first embodiment according to the present invention.
Figure 2:
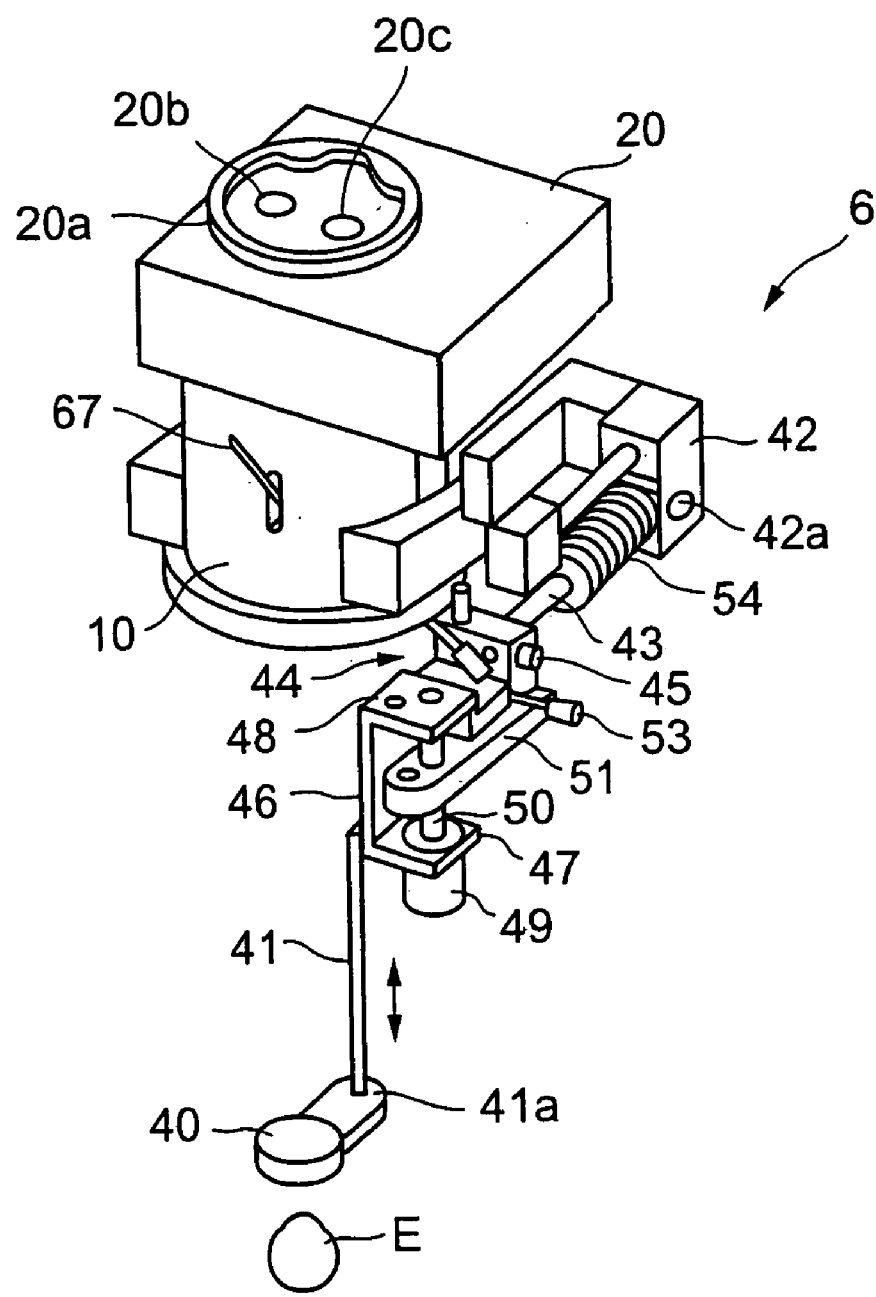
FIG. 2 is a schematic perspective view showing a construction of an operator microscope of the operation microscope of the first embodiment according to the present invention.

Next, a more detailed construction of the operation microscope 1 will be described by also referring to FIG. 2 that is an enlarged perspective view of the operator microscope 6. As shown in FIGS. 1 and 2, the operator microscope 6 includes an objective lens barrel portion 10, an inverter portion 20, one pair of right and left eyepieces 30, a front lens 40, and a holding arm 41 that holds the front lens 40. The holding arm 41 is connected to the objective lens barrel portion 10 through various members to be described later.

(Objective Lens Barrel Portion)

Figure 3A:
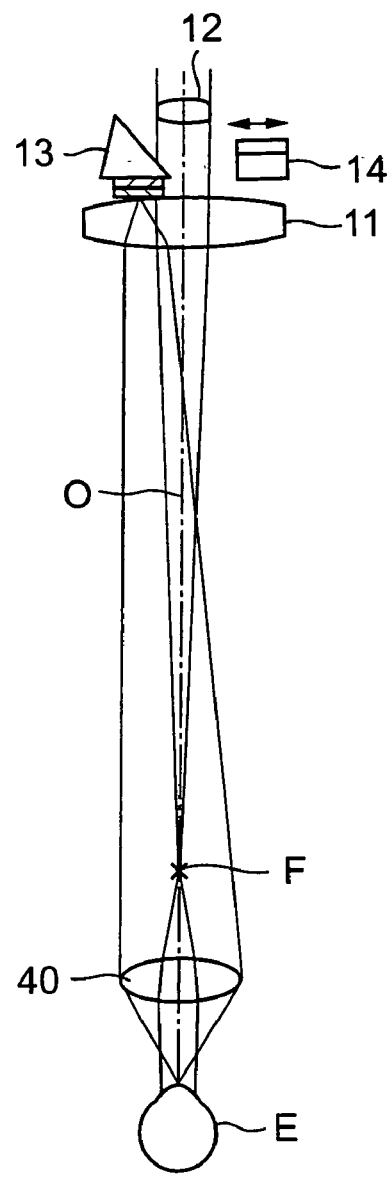
FIG. 3A is a schematic diagram showing a partial construction of an optical system housed in an objective lens barrel portion of the operation microscope of the first embodiment according to the present invention.
Figure 3B:
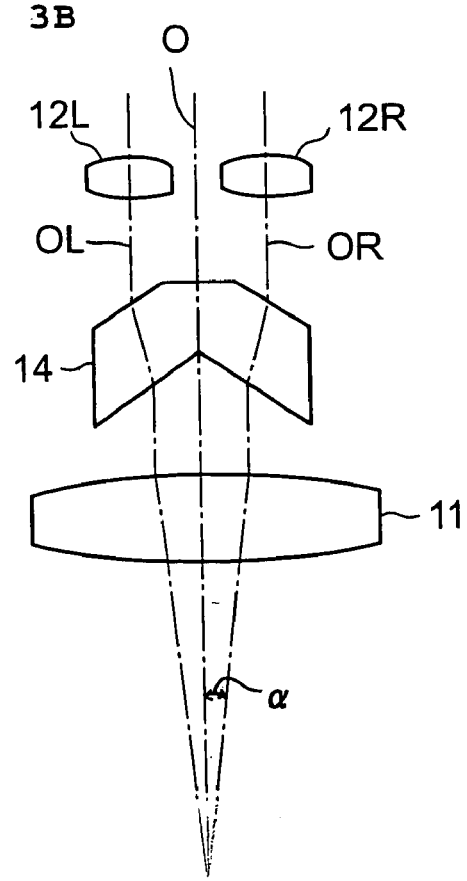
FIG. 3B is another schematic diagram showing the partial construction of the optical system housed in the objective lens barrel portion of the operation microscope of the first embodiment according to the present invention.

FIGS. 3A and 3B each show a partial construction of an optical system embedded in the objective lens barrel portion 10, with FIG. 3A being a side view and FIG. 3B being a front view. Note that in FIG. 3B, the illustration of an illumination prism 13 is omitted and there is shown a state where a stereo variator 14 to be described later is arranged on an optical axis. An objective lens 11 set so as to confront the eye to be operated E, a zoom lens 12, a not-shown light source (see a light source 63 in FIG. 7), the illumination prism 13, and the stereo (angle) variator 14 are housed in the objective lens barrel portion 10. The illumination prism 13 is arranged at a position decentered from an optical axis O of the objective lens 11, and is an optical element for deflecting a light flux emitted from the light source and illuminating the eye to be operated E. Also, the zoom lens 12 is composed of one pair of a right zoom lens 12R and a left zoom lens 12L arranged at positions that are symmetrical about the optical axis O of the objective lens 11, and is one pair of right and left optical systems for guiding a reflection light flux (observation light flux) from the illuminated eye to be operated E to the right and left eyepieces, respectively. Also, the stereo variator 14 is an optical axis position changing element for changing the relative positions of optical axes OR and OL of the observation light flux to be guided by the respective right and left zoom lenses 12R and 12L, and is moved so as to be inserted/removed onto/from the optical path of the observation light flux by a solenoid (optical axis position changing element insertion/removal means) to be described later (driven in an arrow direction shown in FIG. 3A). Here, the light source 63 and the illumination prism 13 constitute an illumination means of the present invention and are set so as to be capable of changing the angle of the illumination light flux illuminating the eye to be operated E with respect to the optical axes OR and OL.

It should be noted here that the objective lens 11 and the front lens 40 are arranged so that the front-side focal position of the objective lens 11 and the rear-side focal position of the front lens 40 coincide with each other (see a point F in FIG. 3A).

(Inverter Portion)

Figure 4:
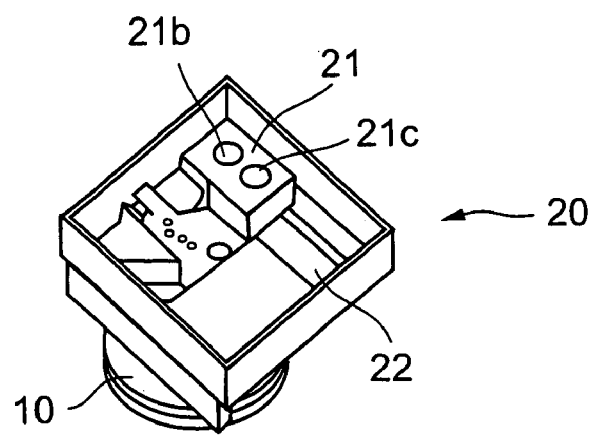
FIG. 4 is a schematic perspective view showing an internal construction of an inverter portion of the operation microscope of the first embodiment according to the present invention.

FIG. 4 shows an internal construction of the inverter portion 20. As shown in this drawing, an optical unit 21 for converting an inverted observation image into an erected image is housed in a casing 20A and is set so as to be movable on a slide rail 22 provided in a bottom portion of the casing 20A. Note that the optical unit 21 is driven by a drive mechanism (optical unit insertion/removal means) to be described later housed in the inverter portion 20 to move along the slide rail 22.

Also, as shown in FIG. 2, a connection portion 20a for attachment of the eyepieces 30 is provided on the upper surface of the inverter portion 20, with an opening portion 20b, through which a light flux to be guided to the eyepiece 30 for the left eye passes, and an opening portion 20c, through which a light flux to be guided to the eyepiece 30 for the right eye passes, being established in the connection portion 20a.

On the other hand, as shown in FIG. 4, an opening portion 21b, through which the light flux to be guided to the eyepiece 30 for the left eye passes, and an opening portion 21c, through which the light flux to be guided to the eyepiece 30 for the right eye passes, are established in the upper surface of the optical unit 21. The position of the optical unit 21 under a state where the opening portion 20b and the opening portion 21b are arranged on a straight line and the opening portion 20c and the opening portion 21c are arranged on a straight line will be hereinafter referred to as the "inverter-on position". On the other hand, the position of the optical unit 21 under a state where it is set at a position other than the inverter-on position will be hereinafter referred to as the "inverter-off position". If the optical unit 21 is set at the inverter-on position, an inverted observation image is converted into an erected image. On the other hand, if the optical unit 21 is set at the inverter-off position, an observation image is recognized as it is. FIG. 4 shows a state where the optical unit 21 is set at the inverter-on position.

(Holding Arm and the Like)

Next, a construction for holding the front lens 40 and inserting/removing the front lens 40 onto/from the space between the eye to be operated E and the objective lens 11 will be described with reference to FIGS. 2, 5, and 6. In a tip end portion of the holding arm 41, a holding plate 41a is formed and the front lens 40 is attached to the holding plate 41a.

A fixing bracket 42 is fixed to the objective lens barrel portion 10 and a supporting rod 43 is attached to the fixing bracket 42 through a rotating shaft 42a serving as an axis. A supporting bracket 44 is fixed to the supporting rod 43 using a fixing screw 45. A holding frame portion 46 of the supporting bracket 44 is formed in a "U-letter" shape having a lower plate 47 and an upper plate 48, with the lower plate 47 being provided with a fine-movement adjustment knob 49 for finely adjusting the position of the front lens 40 in the upward/downward direction (in the arrow direction shown in FIG. 2). Also, a revolving screw 50 is provided between the lower plate 47 and the upper plate 48 and fixes a movable plate 51 to the holding frame portion 46. A base end portion of the holding arm 41 is inserted through a not-shown through-hole established in the supporting bracket 44.

Figure 5:
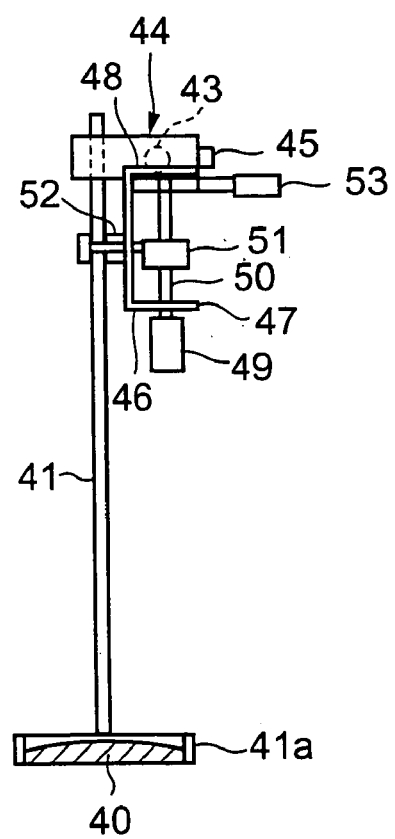
FIG. 5 is a schematic diagram showing a construction for supporting a front lens of the operation microscope of the first embodiment according to the present invention.

As shown in FIG. 5, the movable plate 51 is provided with an arm portion 52 and the holding arm 41 engages with this arm portion 52. When the movable plate 51 is displaced in the upward/downward direction through the rotational movement of the fine-movement adjustment knob 49, the holding arm 41 is also displaced in the upward/downward direction accordingly. In this manner, the front lens 40 is fine by adjusted in its position.

Also, the supporting bracket 44 is provided with a swing lever 53 and the holding arm 41 is set so as to be swingable about the rotating shaft 42a using the swing lever 53. FIG. 6 shows a state where the holding arm 41 is swung and is set under a standing state. It is possible to set the holding arm 41 under the standing state at a received position by retracting the front lens 40 from the eye to be operated E in the case of observing the anterior portion of the eye to be operated E or using a contact lens, for instance. Note that the supporting rod 43 is provided with a coil spring 54 serving as an elastic member for maintaining a used state and a retracted state of the front lens 40.

Figure 6:
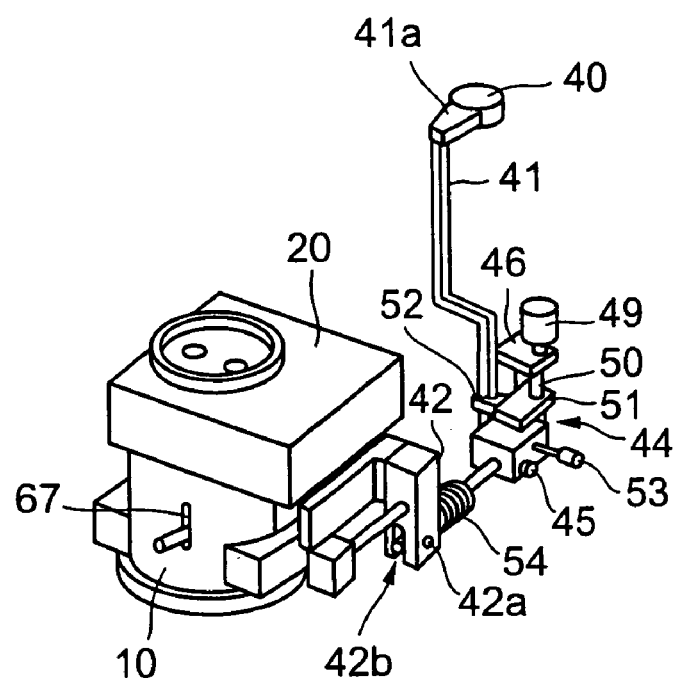
FIG. 6 is a schematic diagram showing a state where a holding arm of the operation microscope of the first embodiment according to the present invention is set under a standing state.

Further, a bearing portion 42b of the fixing bracket 42 for supporting the rotating shaft 42a shown in FIG. 6 is provided with a micro-switch as a detecting means (see a micro-switch 65 in FIG. 7) to be described later. The micro-switch is turned on when the holding arm 41 is lowered and the front lens 40 is set under the used state, and is turned off when the holding arm 41 is swung and the front lens 40 is set under the retracted state. With this construction, it becomes possible to detect whether the front lens 40 is used or retracted.

(Construction Relating to Control)

Figure 7:
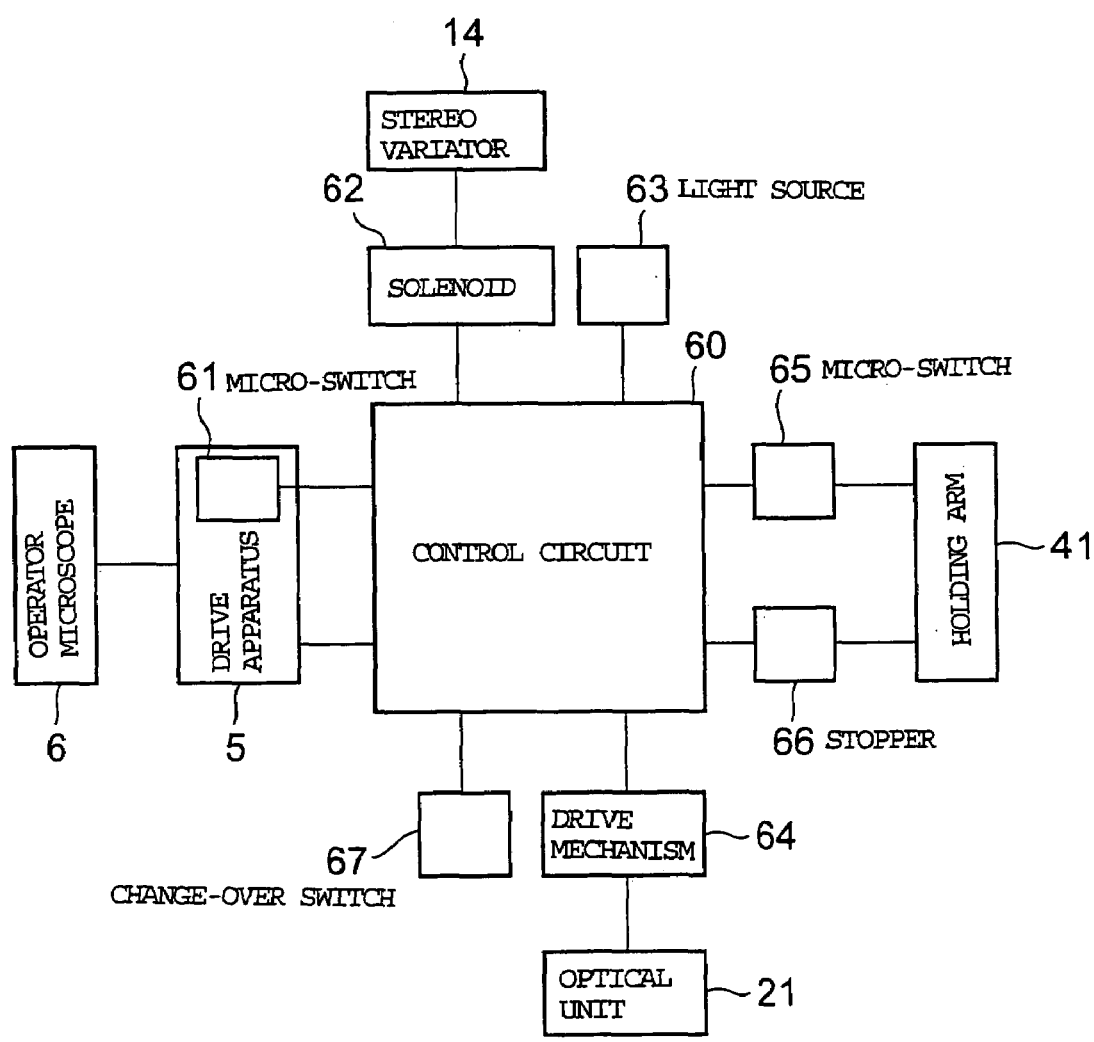
FIG. 7 is a block diagram showing a construction relating to control of the operation microscope of the first embodiment according to the present invention.

Next, a construction for controlling the operation of each portion of the operation microscope 1 will be described by also referring to a block diagram shown in FIG. 7.

The operation microscope 1 is entirely controlled by a control circuit 60 (control means). This control circuit 60 is constructed so as to include a non-volatile storage means, such as a ROM, storing a control program and the like and a computation control means, such as a CPU, that generates a control signal in accordance with the control program stored in the storage means, transmits the control signal to each portion relating to control, and recognizes the state of each portion of the apparatus. The control circuit 60 is housed in the inverter portion 20 of the operator microscope 6, for instance.

The micro-switch 61 described above is provided for the drive apparatus 5 for three-dimensionally driving the operator microscope 6 and judges the arrangement of the operator microscope 6 in the upward/downward direction. Also, the solenoid 62 described above for driving the stereo variator 14 so as to be inserted/removed onto/from the optical path is connected to the stereo variator 14. Further, the light source 63 described above for emitting the illumination light flux for illuminating the eye to be operated E through the illumination prism 13 is provided. This light source 63 is set so as to be capable of changing its turned-on position based on a control signal from the control circuit 60, thereby switching the angle (angle "α" shown in FIG. 3B) of the illumination light flux with respect to the observation optical axis O between 2° and 4°, for instance. Note that the solenoid 62 and the light source 63 operate by power from a not-shown power supply apparatus. Also, the drive mechanism 64 described above that drives the optical unit 21 along the slide rail 22 and performs switching between the inverter-on position and the inverter-off position is connected to the optical unit 21 of the inverter portion 20. Further, the aforementioned micro-switch 65 (detecting means) provided for the bearing portion 42*b* of the fixing bracket 42 detects the use/retraction of the front lens 40 based on the arrangement state of the holding arm 41. It is possible to detect the current state of the front lens 40 by turning on the micro-switch 65 when the holding arm 41 is set under the standing state and the front lens 40 is arranged at the received position and turning off the micro-switch 65 when the front lens 40 is set at a position other than the received position.

In addition, the bearing portion 42*b* is provided with a stopper 66 that prevents the swinging of the holding arm 41 and lifts the prevention. Note that, when a second control mode to be described later is adopted, it is assumed that the stopper 66 prevents the downward swinging of the holding arm 41 in two steps. That is, at a position (hereinafter referred to as the "swing limit position") midway through the changing of the front lens 40 from the retracted state to the used state, the stopper 66 temporarily limits the swinging, lifts this limitation after a predetermined processing is finished, and allows the holding arm 41 to be swung until coming to the used state.

The control circuit 60 recognizes the arrangement of the operator microscope 6 in the upward/downward direction based on the judgment by the micro-switch 61. Also, the control circuit 60 recognizes whether the front lens is set under the used state or the retracted state based on the judgment made by the micro-switch 65. Further, the control circuit 60 controls the operation of each of the drive apparatus 5, the solenoid 62, the light source 63, the drive mechanism 64, and the stopper 66.

In addition, as shown in FIGS. 2 and 6, the objective lens barrel portion 10 of the operator microscope 6 is provided with a change-over switch 67 constituting a switching means of the present invention. The change-over switch 67 is a switch for performing a switching operation of the movement of the operator microscope 6 in the upward/downward direction by the drive apparatus 5. Note that when the front lens 40 is used, the operator microscope 6 is raised and, when the front lens 40 becomes unnecessary and is retracted, the operator microscope 6 is lowered. Here, needless to say, the objective lens 11 and the front lens 40 are attached to the objective lens barrel portion 10, so that when the operator microscope 6 is moved by the movement means 5, the objective lens 11 and the front lens 40 are also moved accordingly.

(Action)

An action achieved by the operation microscope 1 having the construction described above will be explained. As will be described in detail below, this operation microscope 1 is characterized by its construction enabling automatic control and manipulations that should be performed in response to switching between the used state and the retracted state of the front lens 40.

(First Control Mode)

(From Retracted State to Used State)

Figure 8:
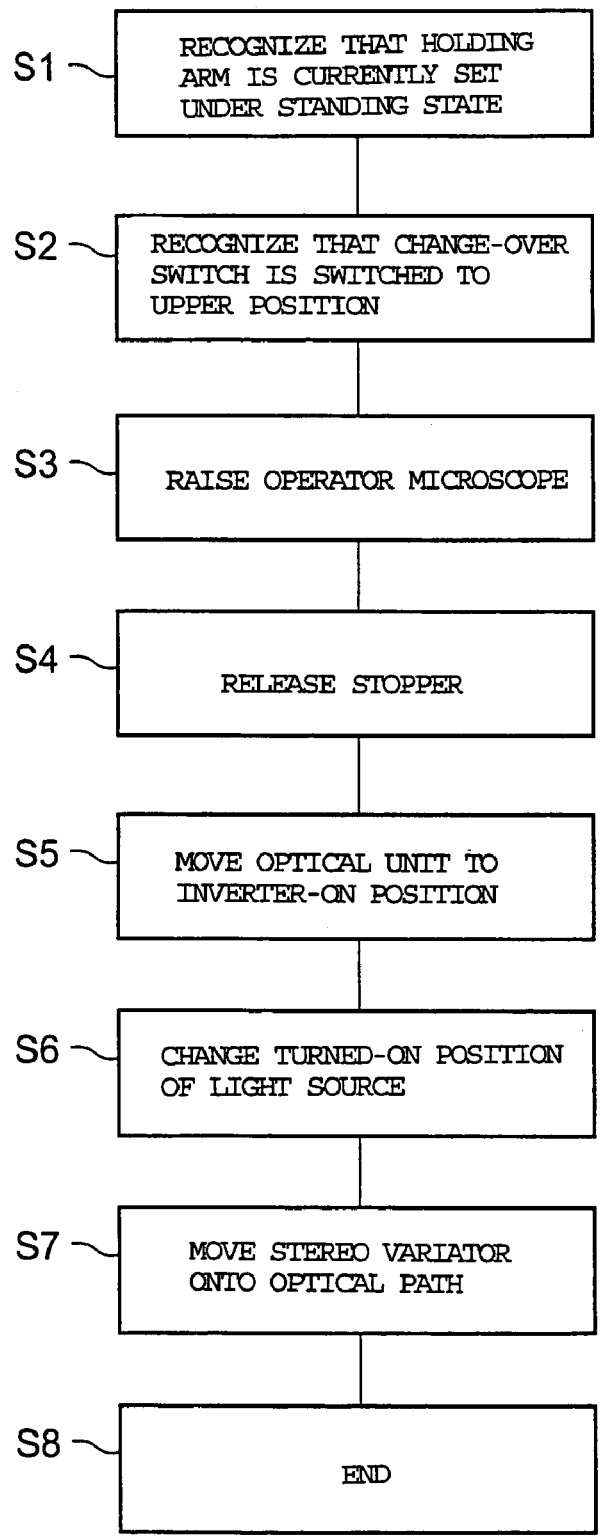
FIG. 8 is a flowchart showing a first control mode of the operation microscope of the first embodiment according to the present invention.

First, an operation of the operation microscope 1 in the case where transition from the observation of the anterior portion of the eye to be operated E to the observation of the retina/vitreous body thereof is performed by switching the front lens 40 from the retracted state to the used state will be described by following a flowchart shown in FIG. 8. When the anterior portion of the eye to be operated E is observed by setting the front lens 40 under the retracted state, the operator microscope 6 is arranged on a lower side, the stereo variator 14 is arranged outside the optical path, the light source 63 is turned on at a position at which the illumination light flux is projected so as to form a small angle α (2°) with respect to the observation optical axis O, and the optical unit 21 is arranged at the inverter-off position. Also, the stopper 66 is activated and prevents the downward swinging of the holding arm 41 and the change-over switch 67 is switched to its lower position as shown in FIG. 6.

First, the control circuit 60 recognizes that the holding arm 41 is set under the standing state and the front lens 40 is set under the retracted state (S1). When recognizing that the change-over switch 67 is switched to its upper position through a manipulation by the operator (S2), the control circuit 60 controls the drive apparatus 5 so that the operator microscope 6 is raised (S3). Also, when recognizing that the operator microscope 6 is raised based on a signal from the micro-switch 61 of the drive apparatus 5, the control circuit 60 performs control so that the prevention of the swinging of the holding arm 41 by the stopper 66 is lifted (S4). As a result, it becomes possible for the operator to swing the holding arm 41 and to arrange the front lens 40 under the used state at a following arbitrary point in time.

Next, the control circuit 60 controls the drive mechanism 64 so that the optical unit 21 is moved to the inverter-on position (S5), changes the turned-on position of the light source 63 so that the illumination light flux forms a large angle α (4°) with respect to the observation optical axis O (S6), controls the solenoid 62 so that the stereo variator 14 is moved and arranged on the optical path (S7), and ends the control processing (S8). Note that it is not necessarily required to perform the control of the solenoid 62, the light source 63, and the drive mechanism 64 in the order shown in the flowchart in FIG. 8 and it is possible to perform this control in an arbitrary order. Further, the interlocking movement (S7) of the stereo variator 14 is not necessarily required.

Here, the downward swinging of the holding arm 41 is prevented by the action of the stopper 66 unless the operator microscope 6 is raised. This is because if the holding arm 41 is swung downwardly under a state where the operator microscope 6 is arranged on the lower side, there is a danger that the front lens 40 may hit the eye to be operated E.

Also, in place of the prevention of the swinging of the holding arm 41 by the stopper 66 (or in addition to the stopper 66), when it is intended to swing the holding arm 41 under a state where the operator microscope 6 is set on the lower side, an alarm sound may be outputted in order to inform the operator of this situation.

(From Used State to Retracted State)

Figure 9:
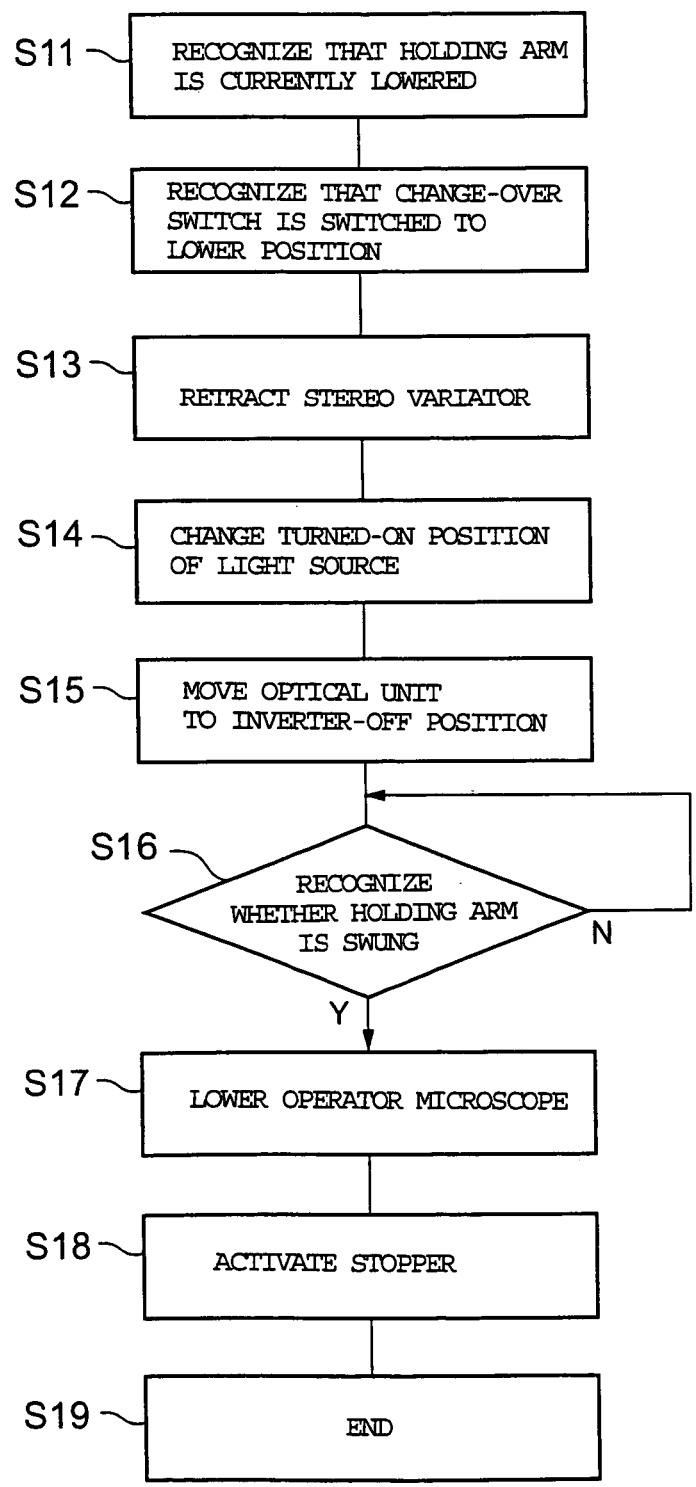
FIG. 9 is another flowchart showing the first control mode of the operation microscope of the first embodiment according to the present invention.

Next, an operation of the operation microscope 1 in the case where the front lens 40 set under the used state is retracted in order to perform transition from the observation of the retina/vitreous body to the observation of the anterior portion will be described by following a flowchart shown in FIG. 9. When the observation of the retina/vitreous body is performed by arranging the front lens 40 under the used state, as can be seen also from the control mode shown in FIG. 8, the operator microscope 6 is set on the upper side, the stereo variator 14 is arranged on the optical path, the light source 63 is turned on at a position at which the illumination light flux is projected so as to form a large angle (4°) with respect to the observation optical axis O, and the optical unit 21 is arranged at the inverter-on position. Also, the change-over switch 67 is switched to the upper position as shown in FIG. 2. Here, the reason why the illumination light flux is projected by a large angle with respect to the observation optical axis is to avoid an influence of the reflection light of the illumination light flux by the cornea on the observation light flux.

First, the control circuit 60 recognizes that the holding arm 41 is lowered and the front lens 40 is set under the used state (S11). When recognizing that the change-over switch 67 is switched to the lower position by the operator (S12), the control circuit 60 controls the solenoid 62 so that the stereo variator 14 is retracted from the optical path (S13), changes the turned-on position of the light source 63 so that the illumination light flux forms a small angle (2°) with respect to the observation optical axis O (S14), and controls the drive mechanism 64 so that the optical unit 21 is moved to the inverter-off position (S15). Here too, like in the above case, it is not necessarily required to perform the control of the solenoid 62, the light source 63, and the drive mechanism 64 in the order described above and it is possible to perform this control in an arbitrary order.

Following this, the control circuit 60 recognizes whether the holding arm 41 is upwardly swung by the operator and the front lens 40 is set under the retracted state based on a signal from the micro-switch 65 (S16). So long as the front lens 40 is set under the used state, the control circuit 60 maintains its waiting state (S16; N). When the holding arm 41 is swung and is set under the standing state (S16; Y), the control circuit 60 controls the drive apparatus 5 so that the operator microscope 6 is lowered (Sl7). Finally, the control circuit 60 prevents the downward swinging of the holding arm 41 by activating the stopper 66 (S18). Then, the control processing is finalized (Sl9).

It should be noted here that the recognition of whether the holding arm 41 is swung is not necessarily performed in step S16, and this recognition may be performed at any other point in time in the course of the control of the solenoid 62, the light source 63, and the drive mechanism 64. Also, control is performed so that the operator microscope 6 is prevented from being lowered unless the holding arm 41 is swung. This is because if the operator microscope 6 is lowered under a state where the front lens 40 is set under the used state, there is a danger that the front lens 40 may hit the eye to be operated E.

Also, in the above description, the holding arm 41 is manually swung by the operator himself/herself. However, a drive mechanism for swinging and driving the holding arm 41 may be provided and the swinging operation may be automatically performed. Note that it is assumed that the automatic swinging is performed at the same timings as in the case of the manual swinging described above.

As described above, in the first control mode, each portion of the apparatus is automatically controlled and a setting appropriate for observation is made in response to switching of the change-over switch 67 for performing upward/downward movement of the operator microscope 6. As a result, manipulations for performing switching between observation methods are simplified thereby avoiding a situation where the operator is bothered by such manipulations.

(Second Control Mode)

Next, another control mode that can be realized by the operation microscope 1 will be described. Note that, in this second control mode, the change-over switch 67 is not used and the micro-switch 65 for generating a signal, with reference to which the arrangement of the holding arm 41 for holding the front lens 40 is recognized, is used as the switching means, as will be described later. When this control mode is adopted, it becomes possible to realize a construction where the change-over switch 67 is eliminated. Also, the stopper 66 prevents the swinging of the holding arm 41 in the two steps, as described above. The second control mode where the construction shown in the block diagram in FIG. 7 is changed in this manner will be described below.

(From Retracted State to Used State)

Figure 10:
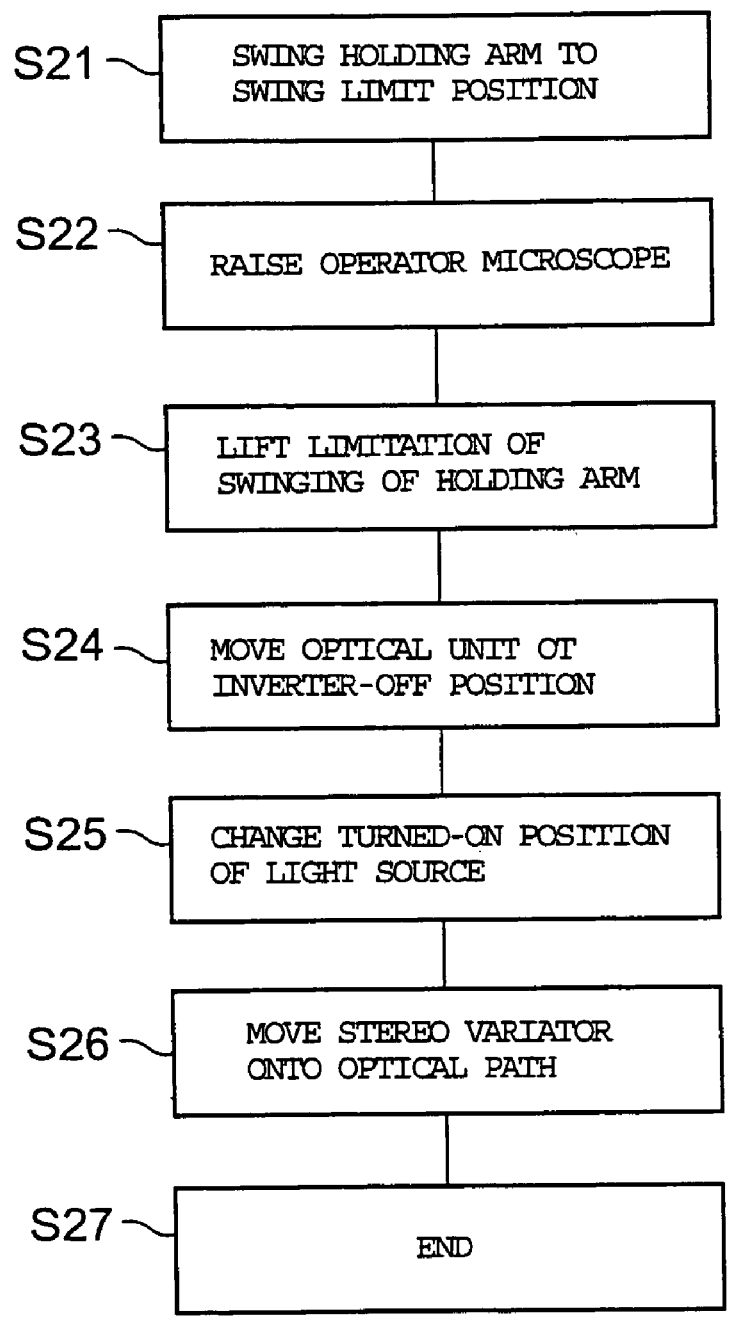
FIG. 10 is a flowchart showing a second control mode of the operation microscope of the first embodiment according to the present invention.

An operation of the operation microscope 1 in the case where the front lens 40 set under the retracted state is changed to the used state will be described with reference to a flowchart shown in FIG. 10.

When the operator swings the holding arm 41 under the standing state to the swing limit position described above (S21), the control circuit 60 controls the drive apparatus 5 so that the operator microscope 6 is raised based on a signal, which shows that the retracted state is cleared, from the micro-switch 65 serving as the detecting means (S22). Next, when recognizing that the operator microscope 6 is raised based on a signal from the micro-switch 61 of the drive apparatus 5, the control circuit 60 lifts the limitation of the swinging of the holding arm 41 by the stopper 66 (S23). Then, the control circuit 60 controls the drive mechanism 64 so that the optical unit 21 is moved to the inverter-on position (S24), changes the turned-on position of the light source 63 so that the illumination light flux forms a large angle with respect to the observation optical axis O (S25), controls the solenoid 62 so that the stereo variator 14 is moved and arranged on the optical path (S26), and finalizes the control processing (S27).

It should be noted here that like in the above cases, it is not necessarily required to perform the control of the solenoid 62, the light source 63, and the drive mechanism 64 in the order described above and it is possible to perform this control in an arbitrary order. Also, by using the swing limit position in S21, it becomes possible to avoid a situation where the holding arm 41 is unexpectedly swung in the downward direction and hits the eye to be operated E. Note that the avoidance of such a situation may be achieved by outputting an alarm sound when the operator microscope 6 is completely raised, for instance.

(From Used State to Retracted State)

Figure 11:
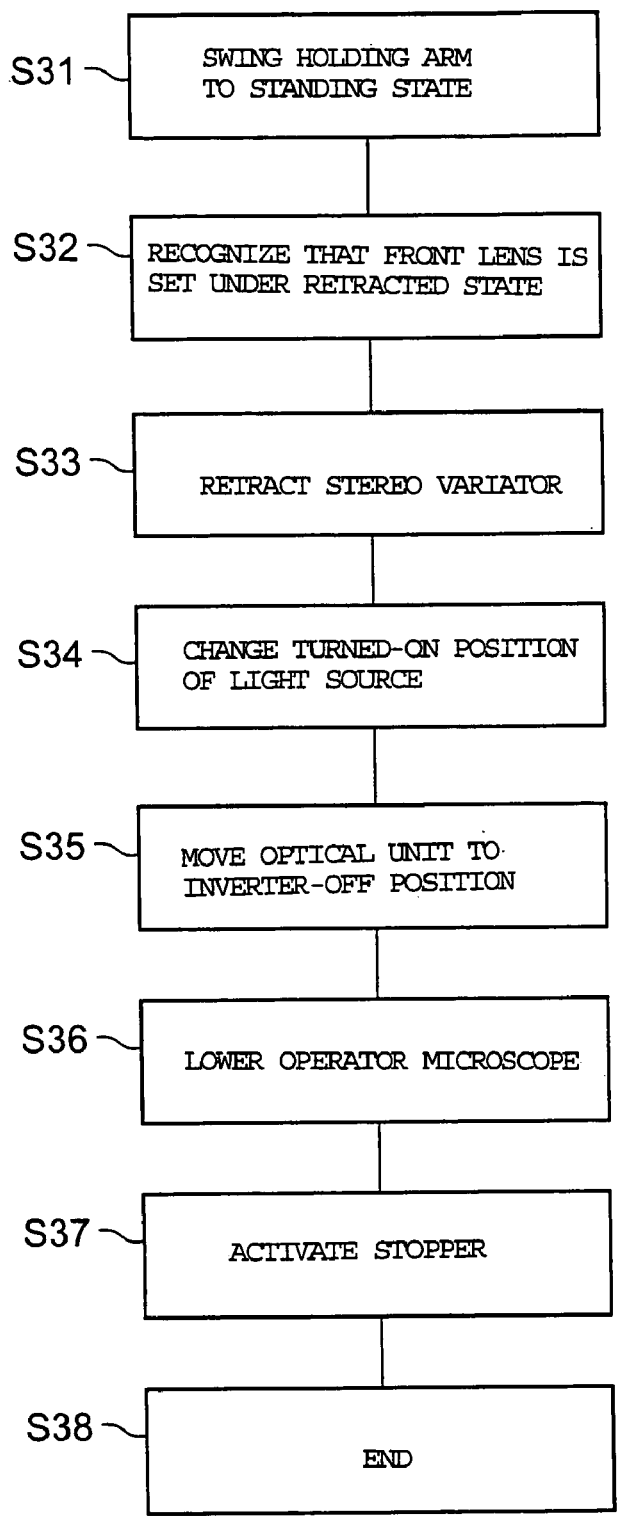
FIG. 11 is another flowchart showing the second control mode of the operation microscope of the first embodiment according to the present invention.

An operation of the operation microscope 1 in the case where the front lens 40 set under the used state is retracted will be described following a flowchart shown in FIG. 11.

When the operator upwardly swings the holding arm 41 to the standing state and sets the front lens 40 under the retracted state (S31), the control circuit 60 recognizes that the front lens 40 is set under the retracted state based on a signal from the micro-switch 65 (S32). Then, the control circuit 60 controls the solenoid 62 so that the stereo variator 14 is retracted from the optical path (S33), changes the turned-on position of the light source 63 so that the illumination light flux forms a small angle with respect to the observation optical axis O (S34), controls the drive mechanism 64 so that the optical unit 21 is moved to the inverter-off position (S35), controls the drive apparatus 5 so that the operator microscope 6 is lowered (S36), and prevents the swinging of the holding arm 41 by activating the stopper 66 (S37). Then, the control processing is finalized (S38). Note that here, like in the above cases, it is not necessarily required to perform the control of the solenoid 62, the light source 63, and the drive mechanism 64 in the order described above and it is possible to perform this control in an arbitrary order.

As described above, in this control mode, the microswitch 65 for recognizing the arrangement of the holding arm 41 serves as the detecting means for switching the setting in accordance with the current state of the front lens 40, that is, use/retraction of the front lens 40.

It should be noted here that the operation microscope according to the present invention may be constructed so as to achieve only one of the first control mode and the second control mode described in detail above. Alternatively, the operation microscope according to the present invention may be constructed so that both of the control modes are prepared and either of them is selectively adopted through a manipulation by the operator or the like.

<Second Embodiment>

(Overall Construction)

Now, an operation microscope of a second embodiment according to the present invention will be described. FIGS. 12A to 12C each show a schematic construction of an operator microscope 106 that is a characteristic portion of an operation microscope 101 of the second embodiment. FIG. 12A is an external side view of the operator microscope 106 and FIG. 12B is an external front view thereof. Also, FIG. 12C is a see-through side view showing a received mode of a front lens. Note that unless differences are specifically described, it is assumed that the operation microscope 101 has the same construction as the operation microscope 1 of the first embodiment. In particular, the operator microscope 106 is capable of being moved upwardly/downwardly by a drive apparatus that is the same as the drive apparatus 5 in the first embodiment. Also, it is of course possible to add various functions of the operation microscope 101 to be described below to the operation microscope 1 of the first embodiment.

Like the operator microscope 6 of the operation microscope 1 of the first embodiment, the operator microscope 106 of this embodiment includes an objective lens barrel portion 110, an inverter portion 120, eyepieces 130, a front lens 140, and a holding arm 141 provided with a holding plate 141a.

The objective lens barrel portion 110 is capable of being finely moved upwardly/downwardly with respect to a main body portion 106a in a range of ±10 mm through a manipulation of a not-shown foot switch, for instance. Also, it is assumed that the moving speed during the upward/downward fine movement is set at around 1 mm per second, for instance. The objective lens barrel portion 110 is provided with an objective lens 111 and a zoom lens 112. It is possible to change the position of the zoom lens 112 using a drive apparatus (drive apparatus 178 in FIG. 13; a zoom magnification changing means) to be described later, thereby changing the zoom magnification of an observation image. Here, the initial position of the zoom lens 112 (initial zoom magnification) is predetermined. It is possible to set the initial zoom magnification at a desired magnification such as a magnification that is most frequently used during actual operations or a magnification at the center of a range of usable zoom magnifications. The initial zoom magnification set in this manner is stored in a storage means of a control circuit 160 (see FIG. 13) to be described later.

Also, on a front surface of the objective lens barrel portion 110, there are arranged a raising switch 167a to be pressed down for upwardly moving the operator microscope 106 and a lowering switch 167b to be pressed down for downwardly moving the operator microscope 106. The raising switch 167a and the lowering switch 167b constitute the switching means of the present invention. Note that the operator microscope 106 is moved by a drive apparatus 105 shown in FIG. 13 to be described later in response to the pressing-down of those switches. The raising switch 167a and the lowering switch 167b are each covered with a detachably attached sterilized cap, thereby preventing a patient from being infected during an operation.

The holding arm 141 and the holding plate 141a are rotatably connected to each other through a rotation shaft 141b. Also, the holding plate 141a is provided with an inclined portion 141c. Further, the holding arm 141 is provided with a front lens manipulation knob 142 for swinging the holding arm 141.

The operator microscope 106 further includes an elevator arm 171 provided with a fringe portion 171a in its upper portion, a connection portion 171b connected to the lower portion of the elevator arm 171, a raising-limit member 172 connected to the connection portion 171b, a coupling knob 173 inserted through the connection portion 171b, and a receiving portion 174 that is detachably attached to the raising degree regulation member 172 and is used for receiving the front lens 140 and the holding arm 141. The holding arm 141 is rotated to the receiving portion 174 through a rotating shaft 174a. Also, a coil spring 154 is attached to the holding arm 141. Note that the reason why the receiving portion 174 is detachably attached to the raising-limit member 172 is that it is required to detach the front lens 140 and the holding arm 141 at the time of sterilization after an operation or the like. Also, even under a state where the front lens 140 and the like are detached, it is possible to use the operation microscope of the present invention as an ordinary operation microscope. In the following description, the construction elements described in this paragraph will be collectively referred to as the "front lens supporting portion" in some cases.

The operator microscope 106 is provided with a drive portion 175 for upwardly/downwardly driving an elevator arm supporting member 176 for supporting the elevator arm 171. The elevator arm 171 is inserted through the elevator arm supporting member 176. Also, the elevator arm 171 is prevented from dropping from the elevator arm supporting member 176 by the fringe portion 171a. With this construction, there is obtained a situation where the front lens 140 is moved upwardly/downwardly by following the upward/downward movement of the elevator arm supporting member 176 by the drive portion 175 and its distance to the objective lens 111 is relatively displaced. Here, the initial position of the front lens 140 is predetermined as a reference position of the upward/downward movement. The initial position is set so that a sufficient distance is maintained between the front lens 140 and the eye to be operated E with consideration given to the safety of a patient. The initial position of the front lens set in this manner is stored in the storage means of the control circuit 160 (see FIG. 13) to be described later. Note that the drive portion 175 constitutes a front lens moving means of the present invention. With this construction, it becomes possible to upwardly/downwardly move only the front lens 140 independently of the upward/downward fine movement of the objective lens barrel portion 110. The displacement degree of the front lens 140 during the upward/downward movement is set at around ±10 mm with respect to the initial position described above, for instance. Also, the moving speed is set at around 1 mm per second, for instance.

Also, in the lower portion of the main body portion 106, a raising limit member 177 for regulating the upward moving range of the front lens supporting portion is attached in addition to the raising limit member 172. In this raising limit member 177, there is established a coupling hole 177a for coupling the front lens supporting portion to the main body portion 106a through a manipulation of the coupling knob 173. Note that the coupling of the front lens supporting portion to the main body portion 106a is performed by raising the front lens supporting portion using the drive portion 175 (setting is made in advance so that a convex portion 173a of the coupling knob 173 is aligned with the coupling hole 177 at this point in time) and then fitting the convex portion 173a into the coupling hole 177a through a rotary manipulation of the coupling knob 173 in a predetermined direction. That is, in the received state of the front lens 140 shown in FIG. 12C, while raising the front lens supporting portion and complying the raising limit member 177 of the main body and the raising limit member 172 provided on the upper portion of the front lens supporting portion, the convex portion 173 is made to be coupled in the coupling hole 177a.

FIGS. 12A and 12B each show a state where the front lens 140 of the operator microscope 106 is inserted into the space between an eye to be operated E and the objective lens 111, that is, a used state of the front lens 140. When the front lens 140 becomes unnecessary and is to be retracted, the operator grabs the front lens manipulation knob 142 and upwardly swings the holding arm 141 about the rotating shaft 174a. Consequently, the front lens 140 and the holding arm 141 are received in the receiving portion 174. On the other hand, when it is desired to set the front lens 140 received in the receiving portion 174 under the used state, the holding arm 141 is downwardly swung in a like manner.

FIG. 12C shows a state where the front lens 140 is received in the receiving portion 174 (received position). In this drawing, the front lens 140 and the holding arm 141 are upwardly swung about the rotating shaft 174a and are received in the receiving portion 174. Also, the holding plate 141a is received under a state where it is rotatively moved about the rotating shaft 141b and is folded. In order to obtain this folded state, in addition to the inclined portion 141c of the holding plate 141a, a contact member 174b is attached to an end portion of the receiving portion 174. With this construction, when the holding arm 141 is upwardly swung, the inclined portion 141c contacts the contact member 174b, the holding plate 141a is rotatively moved about the rotating shaft 141b while being guided by the inclination of the inclined portion 141c, and is automatically folded and received.

Also, in a portion of the receiving portion 174 in which the holding plate 141a is received, a micro-switch 165 as a detecting means is provided which is turned on when the holding plate 141a is received and is turned off when the received state is cleared.

(Construction Relating to Control)

Figure 13:
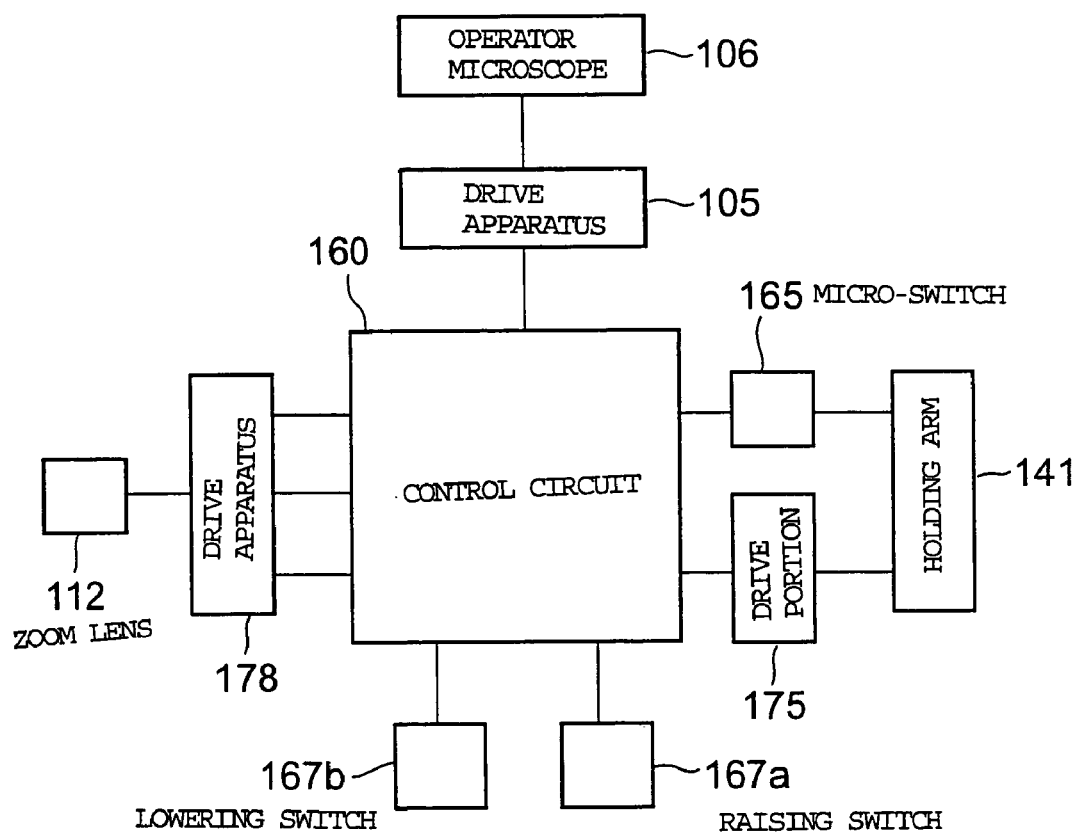
FIG. 13 is a block diagram showing a construction relating to control of the operation microscope of the second embodiment according to the present invention.

FIG. 13 is a block diagram schematically showing a construction for controlling the operation of each portion of the operation microscope 101. The operation microscope 101 is provided with the control circuit 160 for performing control of each portion of the apparatus. Connected to the control circuit 160 are the drive portion 175 provided on a side surface of the main body portion 106a and the micro-switch 165 (detection means) provided for the receiving portion 174. With this construction, the current state (used state/retracted state) of the front lens 140 and the like are detected and each portion is controlled based on a result of the detection. Also, the drive apparatus 178 for changing the zoom magnification by driving the zoom lens 112 is connected to the control circuit 160. Further, the drive apparatus 105 for upwardly/downwardly moving the operator microscope 106 and the raising switch 167a and the lowering switch 167b to be pressed down in order to have the drive apparatus 105 operate are connected to the control circuit 160. With this construction, the operator microscope 101 achieves the action shown in the flowcharts in FIGS. 14 and 15.

It should be noted here that it is of course possible to connect a drive mechanism for driving an optical unit in the inverter portion 120, a light source that is capable of changing the irradiation angle of an illumination light flux, a solenoid for driving a stereo variator, and the like to the control circuit 160, thereby achieving a construction where it is possible to conduct the same control as in the case of the operation microscope 1 of the first embodiment.

(Action)

(From Retracted State to Used State)

Figure 14:
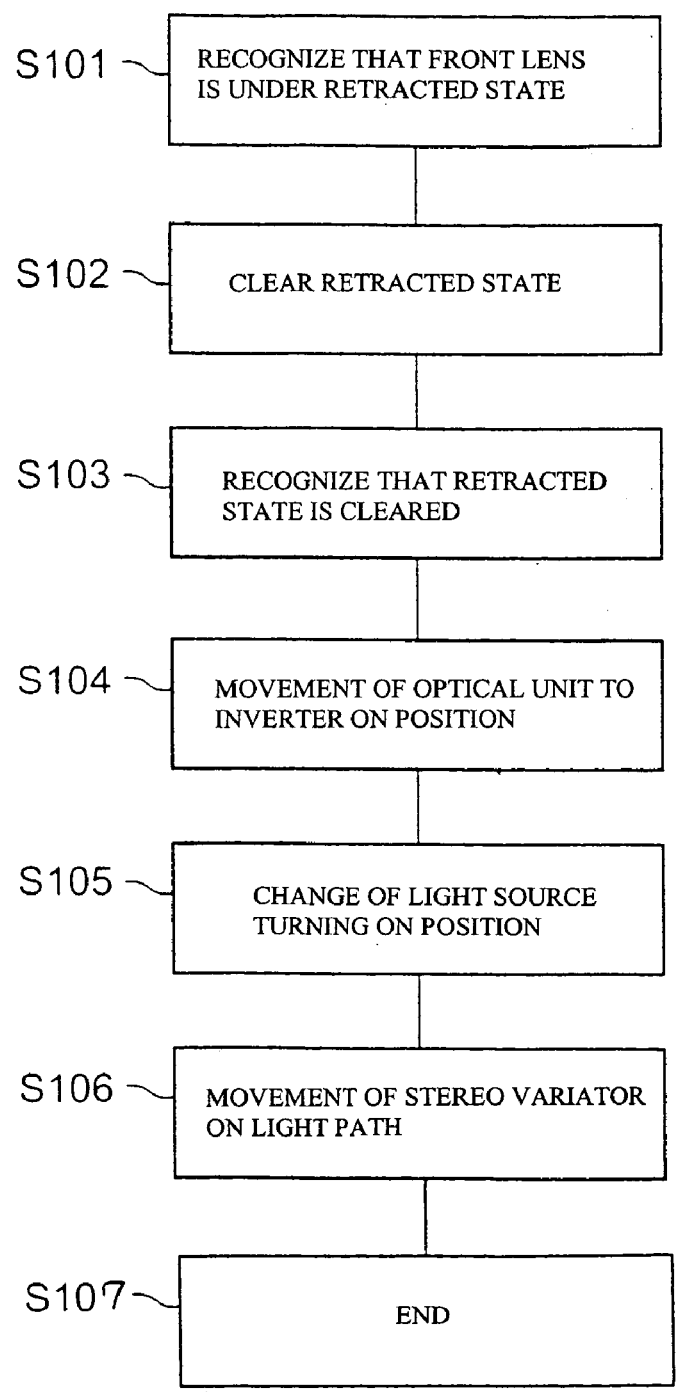
FIG. 14 is a flowchart showing a control mode of the operation microscope of the second embodiment according to the present invention.

A control mode at the time when the front lens 140 transits from the retracted state to the used state will be described with reference to FIG. 14. First, the control circuit 160 recognizes that the front lens 140 is set under the retracted state by checking that the micro-switch 165 is turned on (S101). When the holding arm 141 is downwardly swung using the front lens manipulation knob 142 and the retracted state is cleared (S102), the micro-switch 165 is turned off and the control circuit 160 recognizes that the retracted state is cleared (S103). And the control circuit 160 transmits a control signal to the drive portion 175, which then sets the optical unit to move into the inverter on position (S104). Further, the control circuit 160 changes the turning on position of the light source in order to make the illumination light flux big angle to the observation light axis O (S105). Then, the stereo variator is moved on the light channel (S106), and the control treatment is finalized. Note that it is not necessarily required to perform those process in this order, and it is also possible to perform those operations in an inverse order or at the same time.

(From Used State to Retracted State)

Figure 15:
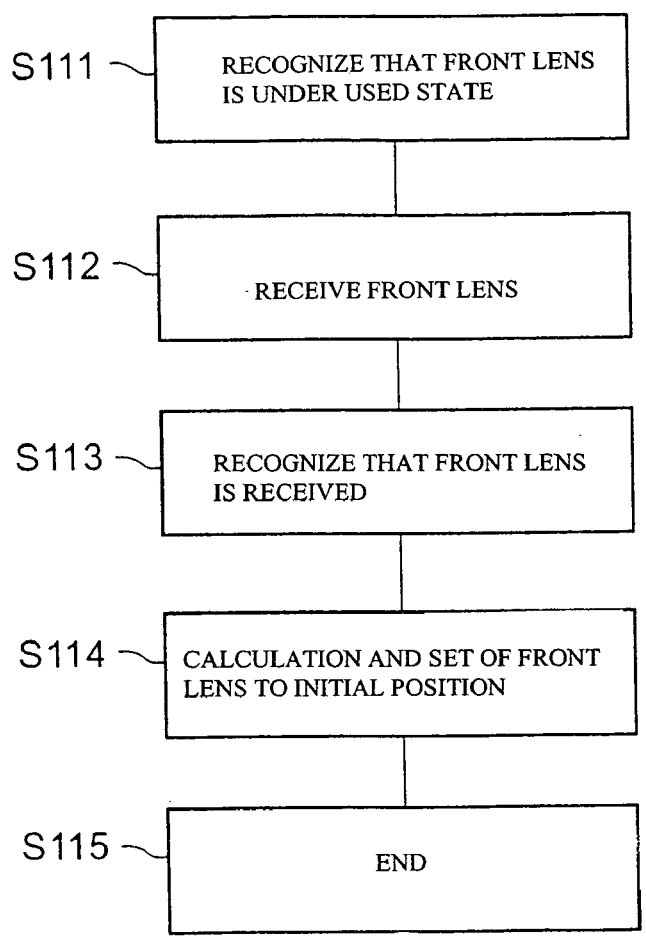
FIG. 15 is another flowchart showing the control mode of the operation microscope of the second embodiment according to the present invention.

Subsequently, a control mode at the time when the front lens 140 transits from the used state to the retracted state will be described with reference to FIG. 15. First, the control circuit 160 recognizes that the front lens 140 is set under the insertion state by checking that the micro-switch 165 is turned off (S111). When the front lens 140 is received in the receiving portion 174 using the front lens manipulation knob 142 (S112), the micro-switch 165 detects this and the control circuit 160 recognizes that the front lens 140 is set under the removal state (S113). After recognizing that the front lens 140 is set under the retracted (received) state based on a result of the detection by the micro-switch 165, the control circuit 160 transmits a control signal to the drive portion 175, which then calculates the front lens 140 at the initial position. That is, when the front lens is received, the distance between the eyepiece and the next use time's position of the front lens is determined to calculate as the initial position. And then, the drive portion 175 is driven to move the elevator arm member 176 upward/downward and the initial position is set (S114). Then, while raising the auxiliary lens supporting portion manually, as described above, keep it contacted to the raising limit member 177. Then, the control processing is finalized (S115).

With the operation microscope 101 described above, when the front lens 140 is inserted/removed and its current state is changed, the initial position of the front lens 140 is automatically calculated. Accordingly, by presetting the initial position and the initial magnification so as to be suited for the contents of an operation or the like, there is eliminated the necessity to manually perform those manipulations each time switching between observation methods is performed during an operation. As a result, it becomes possible to improve manipulability.

In a like manner, it is also possible to interlock the calculating and setting of the initial position of the front lens 140 and the returning in response to the pressing down of the raising switch 167*a* or the lowering switch 167*b*. Also, for instance, control may be performed so that when the micro-switch 165 is turned off (when it is recognized that the front lens 140 is set under the used state), the downward movement of the operator microscope 106 is not performed even if the lowering switch 167*b* is pressed down or control may be performed so that when it is recognized that the received state of the front lens 140 is cleared and the micro-switch 165 is turned off during the downward movement of the operator microscope 106, an alarm sound is outputted. With this construction, it becomes possible to ensure safety for a patient.

Next, a procedure for using the operation microscope 101 that achieves the action described above with the construction described above will be briefly described. Note that as described above, it is possible to add the aforementioned interlocking function of the operation microscope 1 of the first embodiment to the present operation microscope 101.

When transition from the observation of an anterior portion to the observation of an eyefundus or a vitreous body is performed, first, the raising switch 167*a* is pressed down and the operator microscope 106 is upwardly moved only by a predetermined amount (57 mm, for instance). Following this, the holding arm 141 is swung and the front lens 140 received in the receiving portion 174 is set under the used state. In response to the swinging of the holding arm 141 and the setting of the front lens 140 under the used state, the irradiation angle of the illumination light flux is set at a large angle (4°, for instance), the stereo variator and the optical unit are arranged on the observation optical axis, and the lens 140 is returned to the initial position. Note that those interlocked operations may be performed in response to the pressing-down of the raising switch 167*a*. Here, there is a case where the stereo variator is not arranged. Also, before or after the interlocked operations, the coupling state is cleared by rotating the coupling knob 173 and the front lens 140 is lowered to a lower limit position (lowered from the initial position by 10 mm, for instance) by the drive portion 175.

When a flare occurs in an observation image of the eye to be operated, the front lens 140 is adjusted to an appropriate position through upward/downward movement by the drive portion 175. Note that from the viewpoint of elimination of the flare, the adjustment of alignment in the horizontal direction performed at the time of start of an operation is also an important factor. Next, the objective lens barrel portion 110 is upwardly/downwardly fine by moved with respect to the main body portion 106 and is focused on an observation position. As described above, with the operation microscope 101, it is possible to upwardly/downwardly drive the front lens 140 and the objective lens barrel portion 110 independently of each other, thereby allowing the front lens 140 and the objective lens barrel portion to be accurately set, respectively. Note that, when the flare still remains, it is sufficient that the alignment is performed by inserting an illumination filed diaphragm.

When the periphery of an eyefundus is observed through the front lens 140, an eyefundus periphery observation prism is arranged on an upper surface of the front lens 140, alignment in the horizontal direction is performed using the drive apparatus 105, and adjustment is performed so that the illumination light flux strikes the eye to be operated E. Further, if necessary, the flare resolving and the focusing are performed in the manner described above.

During the observation of the periphery of the eyefundus, if it is desired to temporarily observe the anterior portion, an assistant extracts an anterior portion observation lens from a port and inserts it above the front lens 140 by holding the anterior portion observation lens in his/her hand. The insertion position of the anterior portion observation lens is determined by the assistant himself/herself through observation.

When the observation of the periphery of the eyefundus is finished, the holding arm 141 is swung and the front lens 140 is received in the receiving portion 174. In response to those operations, the irradiation angle of the illumination light flux is set at a small angle (2°, for instance), the stereo variator and the optical unit are retracted from the observation optical axis, and the initial position of the lens 140 is calculated. Then, the lowering switch 167*b* is pressed down, the operator microscope 106 is moved downwardly, and the front lens and the like are coupled to the main body portion 106*a* through the coupling knob 173. Note that the interlocked operations performed at the time when the eyefundus periphery observation is finished may be performed in response to the pressing down of the lowering switch 167*b*.

It should be noted here that in the operator microscope 106 of this embodiment, the micro-switch 165 is provided in the receiving portion 174. However, this micro-switch may be arranged at another position so long as it is possible to detect the current state of the front lens 140, that is, whether the front lens 140 is set under the used state or under the unused and received state. For instance, the micro-switch 165 may be provided at a contact portion between the raising-limit member 172 and the raising-limit member 177 used at the time when the holding arm 141 is raised by the drive portion 175 (at the upper surface portion of the raising-limit member 172 or the lower surface portion of the raising-limit member 177). In this case, the micro-switch is turned on when those members contact each other and is turned off when the members are spaced apart from each other. Then, based on the on/off-state of the micro-switch, the current state of the front lens 140 is judged and each portion of the apparatus is controlled in an interlocked manner. In this case, when the raising regulation members 172 and 177 contact each other, the front lens 140 is set at the received position. With the construction described above where the current state of the front lens 140 is detected using the micro-switch and the downward movement is prevented when the front lens 140 is used, it becomes possible to avoid a situation where the front lens 140 hits the eye to be operated E, which enhances safety. Note that it is also possible to perform the control at a desired timing from the start of the retraction of the front lens 140 from between the eye to be operated E and the objective lens 111 to the complete receiving of the front lens 140 at the received position. In addition, the detecting means for detecting the current state of the front lens 140 is not limited to the micro-switch and it is of course possible to use any other detection member so long as it has the same action.

Each control mode described in detail above is an example of the control by the operation microscope according to the present invention. For instance, it is of course possible to perform the control in a mode where any steps of the control processing described above are omitted. Also, an operation microscope having various functions is currently available and it is possible to control each member for achieving the various functions in accordance with whether a front lens is used or retracted.

Also, a manipulation portion for performing selection from among various modes for observing an eye to be operated, such as an anterior portion observation mode, a contact lens use mode, and a retina/vitreous body observation mode, may be provided and a member to be used in the selected mode may be prepared in response to the changing of arrangement of the front lens at the time of transition to the selected mode. With this construction, it becomes possible to automatically make a setting in accordance with which observation mode is selected instead of making a setting in accordance with whether the front lens is used. As a result, it becomes possible to perform control that is more adapted to actual use.

In addition, needless to say, it is possible to make various changes and/or additions to the construction described above without departing from the gist of the present invention.

With the operation microscope of the present invention having the construction described above, it becomes possible to perform a series of manipulations, which should be performed in response to switching between methods for observing an eye to be operated, in an interlocked manner, so that there is eliminated the necessity to manually perform those manipulations during an operation. As a result, manipulability is improved.

Also, with the operation microscope of the present invention, it becomes possible to prevent an accident where the front lens hits the eye to be operated. As a result, it becomes possible to sufficiently ensure the safety of the patient.

What is claimed is:

1. An operation microscope comprising:
   an objective lens set so as to confront an eye to be operated;
   a front lens that is insertable and removable manually from a space between the eye to be operated and the objective lens and having a detecting means to detect the insertion and removal of the front lens;
   an illumination means for generating an illumination light for illuminating the eye to be operated, the illumination means being capable of changing an angle of the illumination light flux with respect to an optical axis of an observation light flux used to observe the eye to be operated; and
   a control means for, based on a signal generated by the operation of the detecting means in response to the insertion and removal of the front lens, operating the illumination means in an interlocking manner so as to observe the eye to be operated.

2. An operation microscope according to claim 1, further comprising:
   a moving means for moving the objective lens and/or the front lens toward the axis direction of the eye to be operated; and
   a switching means for driving the moving means,
   wherein the control means controls, based on the operation of the detecting means, further the switching means and every other means in an interlocking manner with each other so as to observe the eye to be operated.

3. An operation microscope according to claim 2, further comprising:
   an optical unit for, when the front lens is inserted into the space between the eye to be operated and the objective lens, converting an inverted observation image of the eye to be operated into an erected image; and
   an optical unit insertion/removal means for inserting/removing the optical unit onto/from the optical path of the observation light flux from the eye to be operated,
   wherein the control means controls, based on the detecting means, further the insertion/removal of the optical unit onto/from the optical path of the observation light flux by the optical unit insertion/removal means.

4. An operation microscope according to claim 2, further comprising:
   a pair of right and left eyepieces for observing the eye to be operated;
   a pair of right and left optical systems that respectively guide the observation light flux from the eye to be operated to the pair of right and left eyepieces;
   an optical axis position changing element for changing relative positions of optical axes of the observation light flux to be guided by the pair of right and left optical systems; and
   an optical axis position changing element insertion/removal means for inserting/removing the optical axis position changing element onto/from the optical path of the observation light flux,
   wherein the control means controls, in accordance with the current usage state of the front lens, further the insertion/removal ofthe optical axis position changing element onto/from the optical path of the observation light flux by the optical axis position changing element insertion/removal means.

5. An operation microscope according to claim 2, further comprising:
   an optical unit for, when the front lens is inserted into the space between the eye to be operated and the objective lens, converting an inverted observation image of the eye to be operated into an erected image; and
   an optical unit insertion/removal means for inserting/removing the optical unit onto/from the optical path of the observation light flux from the eye to be operated,
   wherein the control means controls, based on the insertion/removal of the front lens, further the insertion/removal of the optical unit by the optical unit insertion/removal means.

6. An operation microscope according to claim 2, further comprising:
   a pair of right and left eyepieces for observing the eye to be operated;
   a pair of right and left optical systems that respectively guide the observation light flux from the eye to be operated to the pair of right and left eyepieces;
   an optical axis position changing element for changing relative positions of optical axes of the observation light flux to be guided by the pair of right and left optical systems; and
   an optical axis position changing element insertion/removal means for inserting/removing the optical axis position changing element onto/from the optical path of the observation light flux,
   wherein the control means controls, based on the insertion/removal of the front lens, further the insertion/removal of the pair of eyepieces, a path of optical systems and the optical axis changing element onto/from the optical path of the observation light flux.

7. An operation microscope according to claim 2, wherein the control means controls, in accordance with the insertion/removal of the front lens, further a direction of the movement of the objective lens and/or the front lens conducted by the movement means with respect to the eye to be operated.

8. An operation microscope according to claim 2, wherein the control means controls so that further the insertion of the front lens into the space between the eye to be operated and the objective lens is prevented until the objective lens and the front lens are moved by the moving means in a direction in which the objective lens and the front lens are drawn away from the eye to be operated.

9. An operation microscope according to claim 2, wherein the control means controls further so that the movement of the objective lens and the front lens conducted by the movement means in a direction, in which the objective lens and the front lens approach the eye to be operated, is prevented until the front lens is retracted from the space between the eye to be operated and the objective lens.

10. An operation microscope according to claim 2, comprising
further a front lens moving means for moving the front lens in an optical axis direction of the observation light flux,
wherein the control means controls, in accordance with the insertion/removal of the front lens, further the front lens moving means so that the front lens is returned to a predetermined initial position.

11. An operation microscope according to claim 2, comprising:
further a zoom magnification changing means for changing a zoom magnification of an observation image of the eye to be operated,
wherein the control means controls, in accordance with the insertion/removal of the front lens, further the zoom magnification changing means so that the zoom magnification is returned to a predetermined initial magnification.

12. An operation microscope according to claim 2, comprising:
further a detection means for detecting whether the front lens is received at a predetermined received position,
wherein the control means controls further the insertion/removal of the front lens based on a result of the detection by the detection means.

13. An operation microscope according to claim 1, comprising:
further a foot switch to operate every interlocking switching means.

* * * * *